United States Patent [19]

Fiechtner et al.

[11] Patent Number: 5,589,393
[45] Date of Patent: Dec. 31, 1996

[54] METHOD FOR PREPARING A GLYCATED HEMOGLOBIN SOLUTION

[75] Inventors: Michael D. Fiechtner, Highland Park; John M. Ramp, Gurnee, both of Ill.; Barbara J. England, Milwaukee, Wis.; Mary J. Annino, Arlington Heights, Ill.

[73] Assignee: Abbott Laboratories, Abbott Park, Ill.

[21] Appl. No.: 427,508

[22] Filed: Apr. 24, 1995

Related U.S. Application Data

[62] Division of Ser. No. 717,558, Jun. 19, 1991, abandoned.

[51] Int. Cl.[6] ................................................. G01N 33/96
[52] U.S. Cl. ........................ 436/15; 436/8; 436/10; 436/16; 436/66; 436/67; 436/826; 356/42
[58] Field of Search ................................ 436/8, 10, 15, 436/16, 66, 67, 826; 356/42

[56] References Cited

U.S. PATENT DOCUMENTS

| | | | |
|---|---|---|---|
| 3,964,865 | 6/1976 | Das . | |
| 3,977,995 | 8/1976 | Louderback et al. . | |
| 4,269,605 | 5/1981 | Dean et al. | 436/67 |
| 4,274,978 | 6/1981 | Moore | 356/40 |
| 4,465,774 | 8/1984 | Huang et al. | 436/15 |
| 4,529,705 | 7/1985 | Larsen | 436/10 |
| 4,590,164 | 5/1986 | Gain | 436/15 |
| 4,649,122 | 3/1987 | Lee | 436/67 |
| 4,800,167 | 1/1989 | Bailey et al. | 436/66 |
| 4,806,468 | 2/1989 | Wagner et al. | 436/67 |
| 4,847,209 | 7/1989 | Lewis et al. | 436/67 |
| 4,861,728 | 8/1989 | Wagner | 436/67 |
| 4,952,520 | 8/1990 | Okusa et al. | 436/824 |
| 5,116,762 | 5/1992 | Vogt et al. | 436/8 |

*Primary Examiner*—James C. Housel
*Assistant Examiner*—Christopher L. Chin
*Attorney, Agent, or Firm*—David L. Weinstein

[57] ABSTRACT

The invention is a rapid, continuous test for glycated hemoglobin using a non-equilibrium affinity binding method. Agarose beads derivatized with 3-aminophenylboronic acid specifically bind glycated hemoglobin. This solid phase is incorporated into a sample processor card, modified to mix and to separate the test solution from the solid phase prior to absorbance readings. Two absorbance readings are made on the test solution, one immediately after mixing the reagent/diluent with the specimen, and one after a significant amount of binding has occurred. A linear correlation between total glycated hemoglobin and hemoglobin $A_{1c}$ permits standardization and reporting of units equivalent to % hemoglobin $A_{1c}$. Stable glycated hemoglobin solutions for use as standards in the assay, and a method for preparing the standards are also disclosed.

8 Claims, 8 Drawing Sheets

METHOD FOR PREPARING A GLYCATED HEMOGLOBIN SOLUTION

This is a division of U.S. Pat. application Ser. No. 07/717,558 filed Jun. 19, 1991, now abandoned and refiled as U.S. patent application Ser. No. 08/431,398.

BACKGROUND OF THE INVENTION

Glycated hemoglobin is a generic term referring to a series of minor hemoglobin components that are formed via the attachment of various sugars, most commonly glucose, to the hemoglobin molecule. The most important of these minor hemoglobin components in respect to diabetes is hemoglobin $A_{1c}$. It is formed by the attachment of glucose to the N-terminal amino acid residue, valine, on one or both β chains of hemoglobin A (Goldstein, D. E. et al. Clin. Chem. 32:B64–B70, 1986).

The human erythrocyte is freely permeable to glucose. Within each erythrocyte, glycated hemoglobin is formed from hemoglobin A (the native, normal form) at a rate proportional to the ambient glucose concentration. The reaction is spontaneous, not enzyme catalyzed, but slow enough that only a fraction of the hemoglobin is modified during the life span of the erythrocyte (120 days) and is irreversible. As a result, glycated hemoglobin provides a weighted "moving" average measure of past blood glucose levels with more recent glucose levels having a greater influence (Singer et al, Ann. Clin. Biochem. 26:213–219, 1989).

Elevated levels of glycated hemoglobin are known to be associated with diabetes mellitus. Glycated hemoglobin is present in non-diabetics at a level of about 5% of total hemoglobin, while diabetics have 2–4 times that amount. Glycated hemoglobin levels are relatively unaffected by short-term (hour-to-hour) fluctuations in blood sugar level and, hence give a relatively precise reflection of the state of blood glucose control in diabetics. The results are indicative of the time-average blood glucose concentration over the past 1 to 3 months. Glycated hemoglobin measurements are used in the assessment of the severity of glucose intolerance in a diabetic patient and in management of diabetes mellitus (Lester, Ann. Clin. Biochem. 26:213–219, 1989; Kennedy et al, Br. Med. Bull. 45:174–190, 1989; Flückiger et al, J. Chromatogr. 429:279–292, 1988; Goldstein, et al., Clin. Chem. 32:B64–70, 1986; Mortensen, Dan. Med. Bull. 32:309–328, 1985; Goldstein et al, CRC Crit. Rev. Clin. Lab. Sci. 21:187–228, 1984; Peacock, J. Clin. Pathol. 37:841–851, 1984; Miedema et al, Ann. Clin. Biochem. 21:2–15, 1984; Mayer et al, Clin. Chem. Acta 127:147–184, 1983; Gabbay, Med. Clin. North Am. 66:1309–1315, 1982).

There are various methods for measuring glycated hemoglobin; as hemoglobin $A_{1c}$ or hemoglobin A1, or as total glycated hemoglobin (ion-exchange chromatography, thiobarbituric acid method, isoelectric focusing, and affinity chromatography assays) (Cole, R. A. et al. Metabolism 27:289–301, 1978; Nathan, D. M. Clin. Chem. 27:1261–1263, 1981; Moore, J. C. et al. Ann. Clin. Biochem. 23:85–91, 1986). In ion-exchange chromatography many glycated hemoglobin species, including hemoglobin $A_{1c}$, are less positively charged at neutral pH than hemoglobin $A_o$, and bind less well to a negatively species, including hemoglobin $A_{1c}$, are less positively charged at neutral pH than hemoglobin $A_o$, and bind less well to a negatively charged resin (Rosenthal, P. K. et al. Am. J. Clin. Pathol. 75:45–49, 1981; U.S. Pat. No. 4,407,961, U.S. Pat. No. 4,649,122). A few methods have been described that separate hemoglobin $A_{1c}$ from hemoglobin $A_{1a+b}$ fraction (Goldstein, D. E. et al. Diabetes 31:70–78, 1982; Maquart, F. X. et al. Clin. Chim. Acta 108:329–332, 1980; Jones, M. D. et al. Hemoglobin 2:53–58, 1978; Clarke, J. T. et al. Diabete Metabol. 5:293–296, 1979; Davis, J. E. et al. Diabetes 27:102–107, 1978; Cole, R. A. et al. Metabolism 27:289–301, 1978; U.S. Pat. No. 4,389,491; Bio-Rad Laboratories, Hemoglobin $A_{1c}$ Micro Column Test Instruction Manual, March 1990). However, these methods suffer from one or more disadvantages. Many of the methods involve the use of two buffers, the first to elute nonbound material from the ion-exchange resin in such a way that does not cause the desorption of the specifically bound material. A second buffer, used at a different pH, ionic strength or containing a competitive inhibitor is needed to elute the specifically bound material. The temperature, pH, ionic strength, and column size affect the test results (Simon, M. et al. Diabetes 29:467–474, 1980; Schellekens, A. P. M. et al. Clin. Chem. 27:94–99, 1981; Castagnola, M. et al. J. Chromatogr. 272:51–65, 1983). Moreover, the methods require several different steps, several vessels, and most of the methods are nonautomated or only semiautomated. Other limitations to these assays, depending on the method used, include a reversible intermediate glycated form, "pre-hemoglobin-A1c", which needs to be removed before the assay is done (Goldstein, D. E. et al. Diabetes 31:70–78, 1982; Bunn, H. F. Diabetes 30:613–617, 1981; Nathan, D. M. Clin. Chem. 27:1261–1263, 1981; Mayer, T. K. et al., Clin. Chim. Acta 127:147–184, 1983; Health and Public Policy Committee, American College of Physicians Ann. Intern Med. 101:710–713, 1984) (Nathan, D. M. Clin. Chem. 27:1261–1263, 1981). High levels of fetal hemoglobin, sickle hemoglobin, and other rarer conditions may interfere with the assay (Niejadlik, D. C. et al., JAMA 224:1734–1736, 1973).

Other methods of determining glycated hemoglobin use specific affinity or binding agents to bind glycated hemoglobin. In the following patents, U.S. Pat. Nos. 4,200,435; 4,260,516; 4,274,978; 4,255,385, and 4,438,204, glycated hemoglobin is determined using affinity methods or the allosteric properties of hemoglobin. In DE Patent 1595 69, a sugar-binding protein as an affinity reagent is described.

Other affinity binding methods are based on specific complex formation between glycated hemoglobin and boronic acid derivatives (Middle et al, Biochem. J. 209:771–779, 1983; Klenk et al, Clin. Chem. 28:2088–2094, 1982; Little et al, Clin. Chem. 32:358–360, 1986, U.S. Pat. No. 4,269,605; U.S. Pat. No. 4,861,728; UK Patent Application GB 2 206 411 A; Isolab, Inc. Technical publication-:Glyc-Affin™ GHb, 1986; Forrest, R. D. et al. Clin. Chem. 34:145–148, 1988). Although affinity binding methods detect glycated hemoglobin species in addition to $HbA_{1c}$, they correlate linearly with methods more specific for $HbA_{1c}$, such as ion-exchange chromatography (Little et al, Clin. Chem. 32:358–360, 1986). Like the ion-exchange and colorimetric assay for glycated hemoglobin, the affinity methods also have Limitations. One of the limitations is that two different buffers are required. The first buffer elutes the non-glycated fraction, which does not have cis-diol groups. The bound fraction, rich in glycated hemoglobin is eluted with a second buffer which contains a displacing agent, such as a sugar alcohol, that displaces glycated hemoglobin from the column. Additionally, the flow rate and size of the column limits the amount of hemoglobin bound to the affinity agent.

There is no consensus on appropriate, stable, glycated standards or calibrators or controls for use in the glycated hemoglobin assays for constructing a standard curve and for determining assay precision (Goldstein, D. E. et al. Clin. Chem. 32,10B:B64–B70, 1986; Franzini, C. et al. G. Ital. Chim. Clin. 9:187–192, 1984). Some of these controls are merely hemolysates of erythrocytes with preservatives added (DD Patent No. 150543; U.S. Pat. No. 3,519,572; GB Patent No. 934461). The materials are often lyophilized and reconstituted in the local laboratory and used over days to weeks (Bio-Rad Laboratories, Hemoglobin $A_{1c}$ Micro Column Test Instruction Manual, March 1990). The stability of these materials has not been well documented. Others have tried to form more stable hemoglobin standards using cyanomethemoglobin; oxyhemoglobin-polyhydroxy compounds, and the carbon monoxide form of hemoglobin (DE Patent No. 3311458; EP Patent No. 72440; and Mosca, A. et al. J. Clin. Chem. Clin. Biochem. 23:361–364, 1985). Many laboratories monitor assay precision by using locally prepared controls, usually hemolysates of whole blood or packed erythrocytes prepared from normal and diabetic samples (Goldstein, D. E. Diabetes 31:70–78, 1982; Cole, R. A. et al. Metabolism 27:289–301, 1978; Simon, M. et al. Clin. Chem. 28:195–198, 1982; Parker, K. M. et al. Clin. Chem. 27:669–672, 1981). These controls must be stored under precisely controlled conditions so that they remain stable (Walinder, O. Clin. Chem. 28:96–99 (1982)).

There is a need for a glycated hemoglobin assay that is easy to perform, free from interferences and relatively insensitive to experimental variables such as pH and temperature. Additionally, there is a need for stable standards and controls for use in such assays as well as a method for preparing the standards.

SUMMARY OF THE INVENTION

The present invention relates to a method for detecting and determining the percent or concentration of a substrate bindable substance in a sample containing the substrate bindable substance to be detected and substrate nonbindable substance. More specifically, the invention relates to a rapid method for detecting and determining the percent or concentration of a substrate bindable substance in a sample containing the substrate bindable substance to be detected and substrate nonbindable substance.

According to the present invention, the absorbance of the sample containing the substrate bindable substance and substrate nonbindable substance is measured and a solid substrate having attached a specific binding or affinity agent is added. The basic components in the binding reaction are, the sample, a solid substrate having attached a binding agent and a buffered solution compatible with the binding reaction.

Following the binding reaction, the absorbance of the sample is determined using a suitable detection device; the amount or proportion of activity in the sample being inversely related to the quantity of bindable substance bound by the solid substrate.

Accordingly, an aspect of the present invention relates to a method for determining the presence and amount of a substrate bindable substance in a sample suspected of containing same, which method entails measuring the initial absorbance of the sample containing substrate bindable and substrate nonbindable substance, binding the substrate bindable substance to a solid support having attached a binding agent specific for the bindable substance, measuring the absorbance of the sample devoid or reduced in the substrate bindable substance, and calculating the percent of the substrate bindable substance.

A preferred aspect of the present invention relates to a method for determining the relative amount of glycated hemoglobin in a sample containing both glycated and nonglycated hemoglobin. A binding or affinity agent that specifically binds glycated hemoglobin is attached to the solid substrate and incorporated in a container modified to mix and separate the particles from the test solution. Two absorbance readings are made on the test solution, one immediately after mixing the reagent/diluent with the test solution, and another absorbance reading after a significant amount of binding of glycated hemoglobin has occurred with the solid substrate. The chemical principle of the assay is based on the affinity binding of cis-diol compounds to 3-aminophenylboronic acid. A linear correlation between total glycated hemoglobin and hemoglobin $A_{1c}$ permits standardization and reporting of units equivalent to % hemoglobin $A_{1c}$.

Another aspect of the invention relates to a method of producing stable liquid glycated and non-glycated hemoglobin solutions for use in a method of determining glycated hemoglobin.

A further aspect of the present invention relates to kits for use in a method of determining glycated hemoglobin.

Another aspect of the invention is to provide a method for determining the percent glycated hemoglobin useful in the diagnosis and monitoring of the diabetic patient.

DESCRIPTION OF FIGURES

These and other objects, features, and many of the attendant advantages of the invention will be better understood upon a reading of the following detailed description when considered in connection with the accompanying drawings wherein.

DETAILED DESCRIPTION OF THE INVENTION

Figure 1:
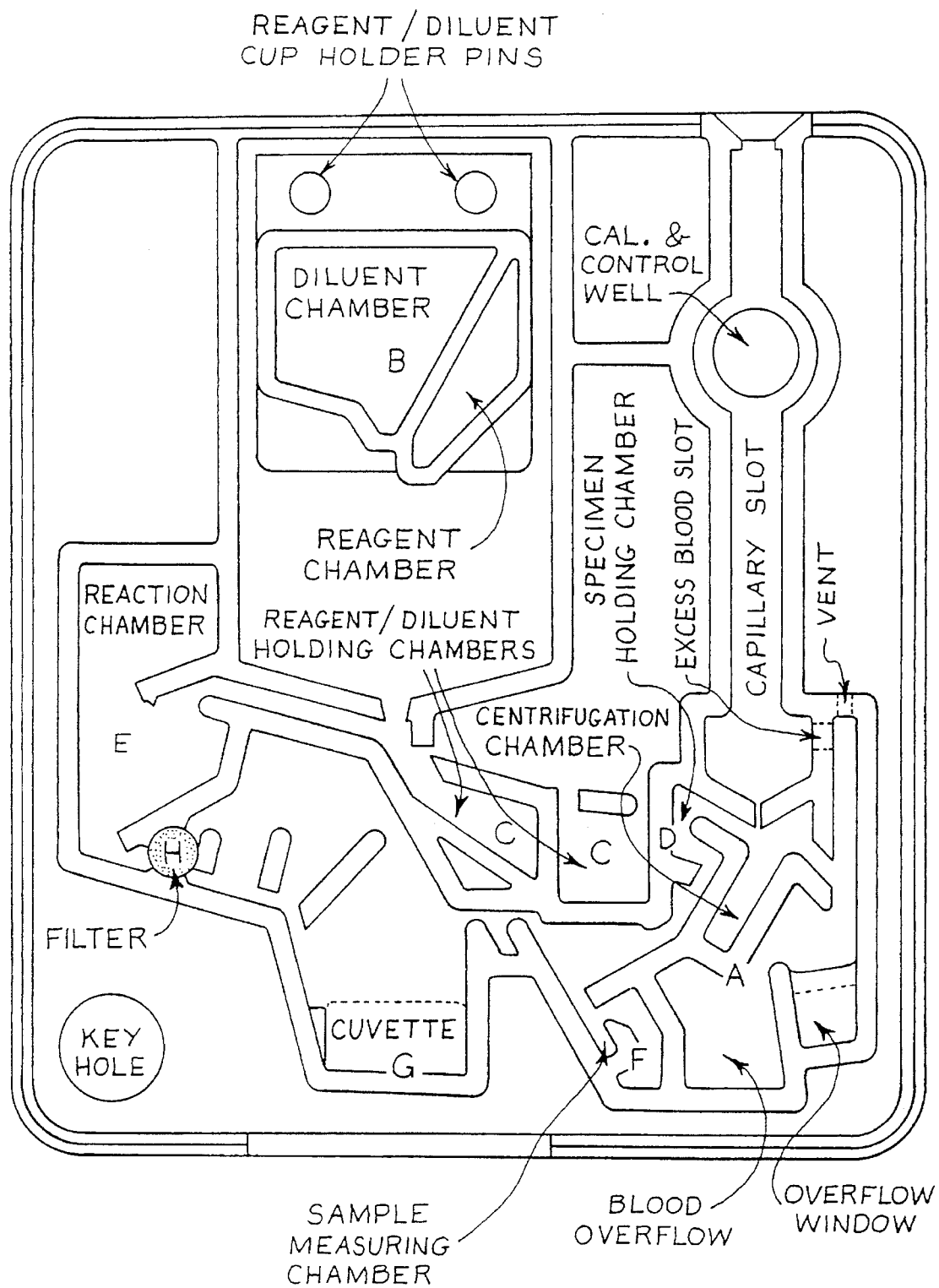
FIG. 1 is a top view of a schematic diagram of the test pack employed in a preferred embodiment of the invention. The details of the test pack are described in U.S. Pat. No. 4,883,763, which has been modified to include a porous filter.

The main problem solved by the present invention was the automation of the process where two absorbance readings are required: one proportional to a total concentration of a bindable substance and nonbindable substance in a sample, the other proportional to either the bound or free fraction subsequent to the binding reaction. The difficulty arises when both readings are taken from a single test solution, within a single test container. This may be done in a system, preferably an automated system, using a self-contained reagent container, without a conventional column chromatograph separation or change in buffers.

One aspect of this invention provides a continuous method, preferably an automated method, for determining the ratio of a substrate bindable substance to the total of the substrate bindable and substrate nonbindable substances in a sample, comprising mixing the sample with a solid substrate, measuring the initial absorbance of the sample containing substrate bindable and substrate nonbindable substance, measuring the absorbance of the sample devoid of the substrate bindable substance, and calculating the ratio of the substrate bindable substance. The solid substrate may comprise particles having attach thereto a binding agent for the substrate bindable substance. The particles are separated from the sample during the measurements of the absorbances. This may be accomplished by several means one of which is by passing a mixture of sample and particles through a porous filter which retains the particles.

The substrate bindable substance may be any molecule which has an affinity for a binding agent. Such bindable substances include carbohydrates, proteins, nucleic acids, lipids and the like. The bindable substances may be derived from animals, plants, bacterial, yeasts, protozoans, viruses, recombinantly produced material and the like. Removal of the substrate bindable substance from a sample should result in a measurable change in the sample which may be detected using an instrument such as a spectrophotometer, fluorimeter or the like. Preferably the measurable change is a change in the optical density of the sample as measured using a spectrophotometer. It is readily appreciated that an amplification system may be needed in order to detect that the substrate bindable substance has been removed or partially removed from the sample. Such amplification systems are known in the art and include enzyme:substrate systems and the like.

One aspect of this invention provides a method for determining the ratio or percent glycated hemoglobin in a sample containing glycated and non-glycated hemoglobin which comprises treating the sample to release the glycated and nonglycated hemoglobin, then contacting a solid substrate with a sample under conditions which effect complex formation between the glycated hemoglobin and the solid substrate and measuring the initial absorbance associated with the total hemoglobin content of the sample, separating the glycated hemoglobin from the sample by binding the glycated hemoglobin to solid substrate, and measuring the absorbance of the sample devoid of glycated hemoglobin or with the glycated hemoglobin greatly reduced.

The present method may be adapted to detect other cis-diol containing substances such as RNA, oligonucleotides, small biological molecules such as catechols including D,L-dopa, epinephrine, norepinephrine or the like, α-hydroxycarboxylic acids such as citrate, lactate, and the like, and other glycated proteins such as albumin and the like. Substances that do not possess the necessary 1, 2-cis-diol structure can often be easily derivatized with polyols which will then enable them to bind to a dihydroxyboryl moiety. For example, most nucleotides and nucleic acids can be coupled via terminal phosphates to sorbitol by treatment with excess sorbitol and 1-ethyl-3(3-dimethylaminopropyl)-carbodiimide (EDC) in 0.5M MOPS buffer pH 5.5 for 2 hours at 25° C. (Boronate Ligands in Biochemical Separation, Publication 501, Amicon Corp., 1981). Deoxyribonucleotides and DNA, which do not ordinarily bind to boronate, can be made to bind tightly if 3' or 5' terminal phosphates are available for polyol derivatization. Derivatized ligands can be restored to the original form by treatment with phosphodiesterase if desired. Methyl-glucamine can be used instead of sorbitol to form a chemically clearable group. Alternatively, a non-cis-diol containing molecule may be bound to a dihydroxylboryl moiety by using a cis-diol containing molecule as a linking agent, provided the cis-diol containing molecule has an affinity for the non-cis-diol containing molecule. Examples of such cis-diol and non-cis-diol binding pairs include; methyl-α-D-glucopyranoside:Concanavalin A; $NAD(P)^+$:glucose-6-phosphate dehydrogenase; ATP:hexokinase; and the like.

The present invention for measuring glycated hemoglobin departs from the prior art in that glycated hemoglobin is determined in a rapid, continuous system that does not require elution of glycated hemoglobin from the solid support. Nor does the present invention require a change in buffers during the assay. Preferably, the system is automated.

Additionally, the present invention provides well defined, stable glycated standards for use as calibrators and controls in assays measuring glycated hemoglobin and the method for preparing the standards.

The principle of the present invention involves affinity binding of glycated hemoglobin to 3-aminophenylboronic acid immobilized on small agarose beads which is measured via bichromatic absorbance at 553/628 nm. An initial absorbance reading proportional to the total hemoglobin concentration is made after mixing of the sample with the reagent and diluent. Complex formation between the coplanar cis-diol groups of glycated hemoglobin (e.g. $HbA_{1c}$) and immobilized 3-aminophenylboronic acid occurs during mixing of the diluted specimen repeatedly with the boronate agarose. This results in removal of glycated hemoglobin from the diluted specimen. A final absorbance reading, proportional to the concentration of [total—glycated hemoglobin], allows the calculation of %Hb bound, which is converted to standardized $\%HbA_{1c}$ using a stored calibration curve.

As a first step a sample must be obtained, preferably a sample suspected of containing glycated hemoglobin, most preferably a whole blood sample. The following specimens are preferred, anticoagulated whole blood prepared using heparin or EDTA. However, specimens collected in sodium citrate and sodium fluoride also can be used. Prior to the determination of glycated hemoglobin in blood samples it is necessary to lyse the erythrocytes. Lysing of the erythrocytes releases both glycated hemoglobin and non-glycated hemoglobin from the cells. Common cationic (e.g., cetyl trimethyl ammonium bromide); anionic (e.g., sodium dodecylsulfate and sodium deoxycholate) and neutral (e.g., saponin and octyl phenoxypolyethoxyethanol) detergents are useful in lysing erythrocytes. Neutral detergents in the concentration range of about 0.025 to 0.5 volume percent are preferred. Mechanical rupture, for example, ultrasonication and hypotonic lysis, are also effective ways of releasing hemoglobin from red blood cells.

To obtain long-term storage stability of the reagents, it may be desirable to add a small quantity of an antimicrobial agent to the system which may include solvents, antibiotics, and poisons. Other biochemicals, e.g., KCN in the determination of glycated hemoglobins, may be introduced to the lysed blood sample.

Next, the sample is treated with a specific binding or affinity agent for glycated hemoglobin to separate the glycated hemoglobin from the non-glycated hemoglobin. In one method, the sample of lysed erythrocytes containing glycated and non-glycated hemoglobins is contacted with a solid substrate having bound thereto a dihydroxyboryl moiety. In another embodiment, the solid support has bound thereto a different binding or affinity agent such as an antibody that has binding specificity for $HbA_{1c}$, or a lectin that specifically binds $HbA_{1c}$.

The solid substrate may take the form of a bead, a resin, or the like. In a particularly preferred embodiment, the solid support is in the form of discrete particles or microparticles. These particles can comprise a natural or synthetic polymeric material which can be cross-linked or not, or chemically modified if desired. Preferably the polymer is hydrophilic in nature such as, a polyacrylamide or an agarose polyacrylamide copolymer such as sold under the trademark Ultragel, or agarose, or a polymer having free hydroxyl groups such as cellulose, cellulose derivatives, starch, dextran and cross-linked dextran, e.g., that sold under the trademark Sephadex, Sepharose, and Sephacryl. The particles can vary widely in diameter, but particles between 40 and 200 μm are preferred.

Particles of this nature lend themselves as a solid substrate for attaching a binding or affinity agent and can be easily used within a container. The container is one in which both the binding between the glycated hemoglobin and the solid support takes places and in which the absorbance is measured. A preferred container is a container in which the particles can be mixed with the test solution and the particles can be separated from the solution during the absorbance readings. The most preferred container is a modification of the solid phase assay device or sample processor card which is described in U.S. Pat. No. 4,883,763, the disclosure of which is incorporated herein by reference. A cylindrical hole in the mixing rib area accommodates a porous filter insert. The filter insert prevents the agarose particles from entering the cuvette and permits the formation of a packed bed of agarose through which the diluted sample flows. Reagent and diluent are precision filled into a double (peel) cup. The dilution ratio is approximately 1:60. Dilution ratio is not critical since the assay does not measure a mass/volume concentration.

Using this solid phase assay device, the particles, contained within the device, have immobilized thereon a specific binding agent for glycated hemoglobin. The particles are retained and immobilized. The sample is mixed with the solid substrate and the glycated hemoglobin is captured and retained on the particles by the reagent on the particles. The non-glycated hemoglobin is not bound by the reagent and thus stays free in solution.

The specific binding agent for glycated hemoglobin may comprise a dihydroxyboryl moiety as described in U.S. Pat. No. 4,269,605 which is incorporated herein by reference. This moiety preferably is phenyl or substituted phenyl boronic acid, boric acid, or other boronic acids, such as ethaneboronic acid, and 1-propaneboronic acid, and the like. The binding agent may be bound to the solid substrate by mechanical, physical or chemical means. Preferably the ligand may be bonded to the matrix by means of a direct covalent bond. The agent should be bound to the substrate in such a way that it does not detach during subsequent reactions leaving boronic acid hydroxyls free. In a preferred method, the affinity resin is prepared by reacting m-aminophenylboronic acid with carboxymethyl-agarose beads (CM-Sepharose™, Pharmacia) activated using 1-ethyl-3-(3-dimethylaminopropyl)-carbodiimide (EDC). Reaction conditions are chosen to yield a product with a controlled degree of substitution in order to maximize specific binding of glycated hemoglobin (GHb) while minimizing the non-specific binding of non-glycated hemoglobin. Regardless of the dihydroxyboryl moiety selected it is required that the sugar moiety of the glycated hemoglobin be bindable to the dihydroxyboryl moiety to achieve the desired separation.

Alternatively, the specific binding agent may comprise an antibody which is coated, immobilized or covalently bound to the particles. Methods for generating antisera by immunization and collection procedures are generally known in the art. The antibody may also be a monoclonal antibody, the procedures for which are also known in the art. An exemplary monoclonal antibody against $HbA_{1c}$ is described by Knowles et al., U.S. Pat. No. 4,727,036.

Another specific binding agent that may be coated, immobilized or covalently bound to particles, include reagents specific for the sugar moieties. These include lectins that have specificity for α-D-glucose including Concanavalin A, Succinyl-Con A, and Vicia faba and the like. Other lectins and their carbohydrate specific fries are well known and available as free lectin or lectin bound to a solid support, e.g. Sepharose™-lectin. Other carbohydrate specific supports include alumina gel, calcium phosphate gel, magnesium carbonate, magnesium silicate and silica gel.

The glycated and non-glycated hemoglobin in a sample are analytically detected and quantified using an apparatus that measures optical density (absorbance) of a solution, preferably a spectrophotometer that is capable of measuring absorbances in the wavelength range of 340 to 633 nm. In a preferred embodiment, the apparatus is an automated Abbott Vision™ Analyzer as described in EP 0 160 901 B1, the disclosure of which is incorporated herein by reference.

The automated analyzer uses the principle of two-dimensional centrifugation to separate plasma from cells, and to measure and mix fluids within the test. pack. Upon initiation of a test, the centrifugal force (1800 rpm platter speed) developed by the spinning platter moves the reagents in the test pack to one or more reagent measuring or holding chambers. At the same time, the specimen is moved from the capillary or specimen well to the blood separation chamber. In the case of anticoagulated hemolyzed whole blood specimen, the centrifugal force causes the lysed red cell stroma to sediment, leaving the hemoglobin containing sample in the upper portion of the chamber. What follows next is a series of rotations by the test pack holder while the platter continues to spin.

The test pack holder rotates the test pack 90° in a counterclockwise direction, causing the buffered reagent and diluent buffer to pour into the reaction chamber and a portion of the specimen to pour into a specimen holding chamber as diagrammed in FIG. 1. The test pack holder then rotates 90° in a clockwise direction, moving the liquid components of the reagent and diluent into the cuvette and moving the specimen to a measuring chamber. The test pack holder then rotates 90° in a counterclockwise direction, moving the measured specimen into the reaction chamber where it mixes with the solid reagent and liquid components of the reagent and diluent coming from the cuvette. A final 90° rotation of the test pack holder in clockwise direction moves the diluted specimen to the cuvette, where the optics system measures the optical density at 553–628 nm for the initial reading and for the final reading after multiple rotations of the specimen with the reagents. The specifications of the Abbott Vision™ Analyzer are described in the Abbott Vision™ Analyzer Manual, p.13.7. Other automated analyzers with similar specifications may be used in the method described.

BUFFERS

The pH is known to affect binding of cis-diol compounds to affinity columns of borate moieties. At high pH values (greater than 9.6) of buffers, hemoglobin binding and stability are reduced whereas, at low pH values, nonspecific binding increases. The nonspecific binding include ionic effects associated with the negatively charged boronate moiety and a hydrophobic component introduced by the phenyl ring. In considering buffers for use in the assay, buffers containing multiple hydroxyl groups such as Tris-(Tris(hydroxymethyl)aminomethane) should be avoided because they bind to the boronate moiety. Sorbitol, serine, ethanolamine, and boric acid should also be avoided. Buffers that serve to strengthen the borate-diol complex formed are preferred. Buffers compatible in this test system are buffers having a pKa in the approximate range of 7.5 to 11.0. Buffers within this range are known in the art. More preferred are buffers with pKa's of approximately 8.5 to 9.2, in order to maintain the pH during the assay in the pH range of approximately 7.8 to 9.6 at 37° C., more preferably between approximately 8.5 to 9.2, most preferably in the range of 9 to 9.2. Amines may serve to strengthen the complex, thus buffers such as glycine, morpholine, HEPES, or additives such as ammonium salts or piperidine may be advantageous to promote binding. In a preferred embodiment, the buffer used to maintain the pH is 2-aminoethylsulphonic acid (taurine), which has a pKa of 9.06, in a concentration of 20 to 50 mM, preferably 25 mM.

Middle, F. A. et al Biochem. J. 209:771–779 (1983) and Boronate Ligands in Biochemical Separations, Publication 501, Amicon Corporation (1981) describe the use of divalent cations, primarily $Mg^{2+}$ derived from $MgCl_2$ to overcome the repulsion between the negatively charged immobilized boronate and negatively charged ligands. The present invention also uses $Mg^{2+}$ for this purpose. However, the present invention preferably uses $MgSO_4$ instead of $MgCl_2$, which allows the invention to operate optimally. The preferred concentration of $MgSO_4$ is approximately 10–500 mM, more preferably 50–200 mM, and most preferably about 100 to 150 mM. Hemoglobin is marginally stable at 37° C. and elevated pH. Running the assay in the presence of chloride, an absorbance decrease of about 8% results, in the absence of any boronate agarose. This is attributed to a combination of precipitation and adsorption to the plastic surfaces of the test pack. An 8% decrease in absorbance is about twice the signal expected for a sample with a normal glycated hemoglobin level, in the absence of any non-specific loss would be about twice the size of the signal. Substituting $MgSO_4$ of hemoglobin from the solution. In other words, the background for $MgCl_2$ was found to decrease this loss to about 3%.

Additional stabilization of the hemoglobin was achieved by incorporating gelatin (fish scale) and polyvinylpyrrolidone (PVP) in the buffer. In combination with $MgSO_4$, this decreases the loss to about 1%. Data from this experiment are shown in Table 1. Other proteinaceous stabilizers, such as casein, gelatin from other sources, albumin and the like, and water soluble polymers may also be expected to give similar results.

TABLE 1

REFORMULATION OF BUFFER*:REPLACING $MgCl_2$ WITH $MgSO_4$

| "STABILIZERS" | | % SIGNAL LOSS | |
|---|---|---|---|
| | | CHLORIDE | SULFATE |
| NONE | | 8.3 | 2.9 |
| GELATIN | 0.5% | 5.8 | 1.1 |
| | 1% | 4.7 | 0.9 |
| | 2% | 5.0 | 0.9 |
| PVP | 0.5% | 5.5 | 0.9 |
| | 1% | 4.8 | 0.8 |
| | 2% | 4.2 | 0.7 |

*Buffer = 25 mM Taurine, 100 mM $Mg^{2+}$, pH 9.2, 22° C.
Sample = Azido-met hemoglobin (non-glycated)

ASSAY

For the purpose of the assay, a measured amount of solid substrate (ranging from 10 to 200 μl, typically 65 μl) is supplied either as a dry tablet or a wet suspension, along with a suitable amount of buffer solution. The buffer solution contains 20 to 50 mM of a compound with a pKa suitable for maintaining the pH of the reaction at a fixed value in the range from about 8.5 to 9.2 upon addition of a blood sample. The addition of a $Mg^{++}$ salt to the buffer at a fixed concentration of approximately 10 and 500 mM, more preferably between about 50 and 200 mM, most preferably between about 100 and 150 mM overcomes electrostatic repulsion between GHb and the boronates on the solid substrate. Protein stabilizers to prevent hemoglobin precipitation and anti-microbial preservatives may also be included in the buffer. The assay temperature is approximately 24° C. to 39° C., more preferably in the range of about 30° C. to 37° C., and most preferred is a temperature of approximately 37° C.

The blood sample is initially treated with heparin to prevent clotting and saponin to lyse the red blood cells. The sample is then centrifuged and an aliquot of the sample is briefly mixed with the resin and buffer. The diluted sample is separated from the resin and an initial absorbance of the diluted sample is obtained. The diluted sample is then extensively mixed with the resin until a substantial amount of the glycated hemoglobin is bound to the solid to the solid support. The resin is removed and a final absorbance reading is taken. The absorbance data are processed to calculate the relative amount or percent hemoglobin bound. The percent glycated hemoglobin is determined from a standard curve of hemoglobin bound versus percent glycated hemoglobin. The standard curve is prepared by the same process using calibrators of known percent glycated hemoglobin. Controls of known percent glycated hemoglobin are used to periodically test or confirm the viability of the standard curve over time.

GLYCATED HEMOGLOBIN DATA REDUCTION

The following steps are performed by the analyzer in order to construct a standard curve and read unknown samples off the curve. An initial absorbance reading ($A_i$) proportional to the total hemoglobin concentration, and a final absorbance reading ($A_f$) proportional to (total—unbound) hemoglobin are taken and stored. The observed % hemoglobin bound (%B) is calculated using the following equation:

$$\%B = 100 \times (A_i - A_f)/A_i$$

This % bound must be corrected for two effects: 1. Some binding takes place prior to the initial reading. 2. The final reading is taken before equilibrium is reached. As a consequence, the observed % bound is affected by the total hemoglobin concentration. Observed % bound increases with decreasing hemoglobin concentration. Therefore, the corrected % bound (%D) is obtained by adjusting the observed % bound using a pair of constants (E and I) and the initial absorbance reading ($A_i$):

$$\%D = \%B - E \times (A_i - I)$$

I is equal to the initial absorbance reading obtained with a specimen of "normal" hemoglobin at a concentration of approximately 13 g/dl. This parameter is dependent on the actual measurement wavelength, the dilution factor in the test pack, and the pathlength of the cuvette in the test pack. One of two alternative values of I is selected depending on whether the sample is a calibrator/control or patient specimen. The dilution factor and pathlength are controlled in test pack manufacture. The actual measurement wavelength varies somewhat from instrument to instrument. Therefore, a unique pair of I's is used for each instrument. E is a constant empirically derived by determining the bound as a function of hemoglobin concentration, while maintaining the % glycation constant. One of two alternative values of E is selected depending on whether the sample is a calibrator/control or patient specimen.

A linear standard curve is calculated from regression analysis of %D vs %$HbA_{1c}$ for calibrators with assigned values of %$HbA_{1c}$.

$$\%HbA_{1c} = (m \times \%D) + B$$

where m is the slope and B is the Y intercept.

Example: Standard curve:
% HbA1c = (0.8741 × % D) + 0.996
E = 7.7 × $10^{-4}$    I = 1500

| Hb Conc. (g/dl) | Ai (mA.U) | % B | % D | % $HbA_{1c}$ |
|---|---|---|---|---|
| 17.0 | 1962 | 8.82 | 9.18 | 9.02 |
| 15.0 | 1731 | 9.00 | 9.18 | 9.02 |
| 13.0 | 1500 | 9.18 | 9.18 | 9.02 |
| 11.0 | 1269 | 9.36 | 9.18 | 9.02 |
| 9.0 | 1038 | 9.54 | 9.18 | 9.02 |
| 7.0 | 808 | 9.71 | 9.18 | 9.02 |

Figure 2:
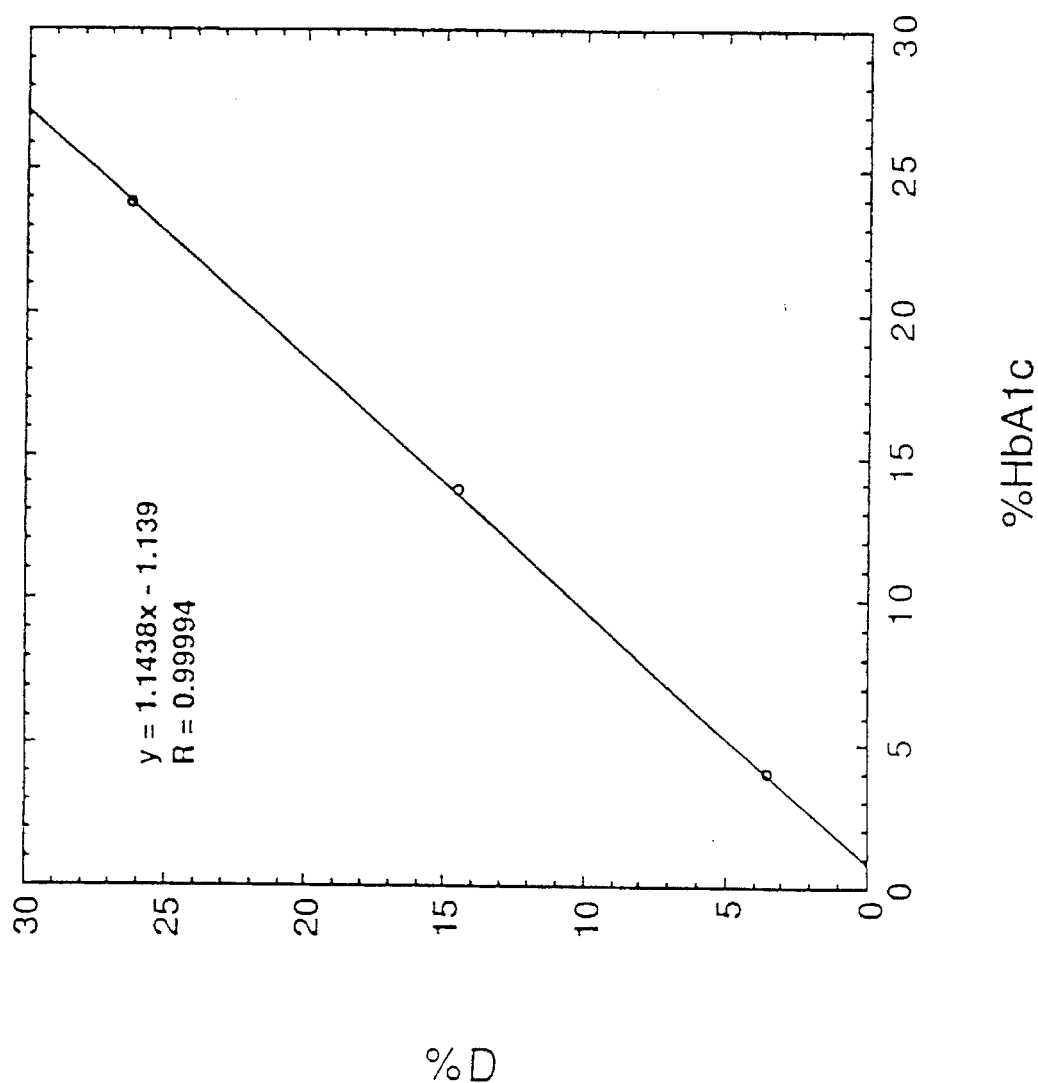
FIG. 2 is a glycated hemoglobin standard curve using bovine azido-met-hemoglobin calibrators as determined by the method of the present invention on an Abbott Vision™ analyzer.

The standard curve is plotted in FIG. 2. Using this data reduction method allows the accurate determination of %$HbA_{1c}$ in specimens of widely varying hemoglobin concentration. One potential advantage is that specimens of limited volume (e.g. neonatal) can be diluted and still be analyzed accurately.

CALIBRATOR/CONTROLS

The glycated hemoglobin calibrators and/or controls for use in glycated hemoglobin assays are preferably liquid materials prepared from human or animal blood. In one embodiment, the glycated hemoglobin material is prepared from bovine erythrocytes. The glycated hemoglobin calibrators preferably contain low, intermediate, and high levels of glycated azido-met-hemoglobin (Example 3), preferably in the reduced form, in a buffer solution at a pH of approximately 5–9 and more preferable 6–8. The level of glycated hemoglobin material contained in the calibrators can be represented by either percent total glycated hemoglobin (TGHb) or percent hemoglobin ($HbA_{1c}$), which is the amount of glycated hemoglobin or hemoglobin $A_{1c}$ relative to the total amount of hemoglobin in the sample. The low calibrator range from approximately 0%–10% TGHb or 0%–8% $HbA_{1c}$, more preferably approximately 2%–7% TGHb or 3%–6% $HbA_{1c}$, most preferably 4%–5% TGHb or $HbA_{1c}$. The intermediate calibrator may range from approximately 10%–27% TGHb or 8%–16% $HbA_{1c}$, more preferably 13%–21% TGHb or 10%–15% $HbA_{1c}$, most preferably from approximately 15%–18% TGHb or 11%–13% $HbA_{1c}$. The high calibrator may range from approximately 22%–44% TGHb or 16%–30% $HbA_{1c}$, more preferably 26%–36% TGHb or 18%–25% $HbA_{1c}$, most preferably from approximately 27%–30% TGHb or 19%–21% $HbA_{1c}$. The low, intermediate, and high calibrators may be formulated from admixtures of a stock solution of glycated hemoglobin material in a percent glycation range of preferably greater than 4%–5% TGHb or 30% $HbA_{1c}$, more preferably from approximately 45%–60% TGHb or 30%–40% $HbA_{1c}$ and a non-glycated reduced hemoglobin solution. The non-glycated hemoglobin solution may contain minimal amounts of glycation.

The stability of the calibrators and controls should be approximately greater than 10 months when stored approximately at or below 8° C., more preferably in the range of 10–14 months, and most preferably with a stability of at least 14 months.

The controls are prepared in the same manner as the calibrators. The control levels are preferably selected to reflect the normal (4%–6% $HbA_{1c}$) and elevated (greater than 8% $HbA_{1c}$) physiological levels of glycated hemoglobin.

In one embodiment of the invention, stable hemoglobin solutions are prepared from azido-met-hemoglobin. Azido-met-hemoglobin can be prepared from lipid free hemoglobin released from washed erythrocytes by hypotonic shock. The source of the erythrocytes is from humans or animals, preferably mammals, and more preferably from bovine erythrocytes. The hemoglobin is oxidized to met-hemoglobin with an oxidizing agent, such as potassium ferricyanide, sodium nitrate or the like. The met-hemoglobin is then converted into azido-met-hemoglobin upon exposure to an azide salt, such as sodium azideor the like.

Hemoglobin in erythrocytes becomes glycated in the presence of glucose by a nonenzymatic process. Initially, a readily reversible reaction takes place between glucose and the N-terminal valine of the beta-chains of hemoglobin to form a labile aldimine or Schiff base. This rapid equilibrium is followed by a slow Amadori rearrangement to form the stable ketoamine linkage of hemoglobin $A_{1c}$. Measurement of hemoglobin $A_{1c}$ is a useful indicator of long-term diabetic control.

In another embodiment of the invention, stable glycated hemoglobin solutions are prepared from azido-met hemoglobin. The nonenzymatic hemoglobin reaction was used for the in vitro synthesis of stable liquid glycated hemoglobin calibrator and control material. Azido-met-hemoglobin from human or bovine erythrocytes was incubated preferably at 37° C. for several days with various concentrations of glucose. The glucose molecules form a Schiff base species with amine groups on the hemoglobin. After removal of unreacted glucose, the labile Schiff base species were stabilized by reduction with a mild reducing agent, such as sodium cyanoborohydride, catalytic hydrogenation in the presence of a catalyst, such as palladium or the like, sodium borohydride, or the like. The completion of the reduction may be tested by heatstressing the reduced glycated azido-met-hemoglobin at elevated temperatures, such as at approximately 45° C. Reduction by-products were removed by gel filtration or dialysis.

The concentration of glucose added to the azido-met-hemoglobin to form glycated hemoglobin is approximately 50–1000 mM, preferably between about 100–500 mM, and most preferably in the approximately range of 150–300 mM. The glucose is incubated with the azido-methemoglobin for approximately 1–10 days or until the desired percent glycation is reached.

In yet another embodiment, a cyano group can be used in place of the azido group. Cyano-met-hemoglobin and reduced glycated cyano-met-hemoglobin will also form stable hemoglobin and glycated hemoglobin solutions. The preparation method for azido-methemoglobin and reduced glycated azido-met-hemoglobin can be utilized to prepare cyano-met-hemoglobin and reduced glycated cyano-met-hemoglobin. A cyanide salt, such as sodium cyanide, is simply used in place of the azide salt in the preparation method.

In yet another embodiment, a carbonyl group can be used in place of the azido group. Carbonyl-hemoglobin and reduced glycated carbonyl-hemoglobin will also form stable hemoglobin and glycated hemoglobin solutions. The preparation method for carbonyl-hemoglobin involves bubbling carbon monoxide gas into the oxyhemoglobin solution prior to glycation. In this case potassium ferricyanide or other oxidizing agents are not required, since oxyhemoglobin is the preferred precursor for carbonyl hemoglobin formation. An anti-foaming agent may be required to minimize foaming during the carbon monoxide bubbling process. The resulting carbonyl-hemoglobin material is glycated and processed in the same manner as the azido-met-hemoglobin or the cyano-met-hemoglobin.

KITS

The present invention also includes test kits for use in assaying glycated hemoglobin content of a sample, preferably a blood sample containing glycated and nonglycated hemoglobin. The test kit includes the following components: (1) a buffered reagent solution with a pH of approximately 6 to 8, preferably 7.7, containing a suspension of particles having attached thereto a binding agent for glycated hemoglobin, preferably a dihydroxyboryl moiety, more preferably 3-aminophenylboronic acid, and a $Mg^{2+}$ source, and (2) a diluent buffer solution capable of maintaining the pH of the reaction mixture in a range between about 7.8 to 9.6, more preferably 8.5 to 9.5, and most preferably 9 to 9.2 at 37° C., the buffer having a pKa of approximately 7.5 to 11, preferably a pKa of 8.5 to 9.2. Depending on the particle material and binding agent used in the test, the test kit components may be supplied separately or in combination, or may be pre-mixed and supplied as one solution mixture.

In another embodiment, the affinity particles have attached an anti-glycated hemoglobin antibody or a lectin as the binding agent.

More preferably the buffered reagent solution contains dihydroxyboryl derivatized particles, approximately 10 to 500 mM $MgSO_4$, most preferably approximately 100–150 mMbMgSO$_4$. The buffered reagent solution may additionally contain an antimicrobial agent and or preservatives, such as gentamicin, sodium azide and the like.

Most preferably the buffered reagent solution contains a suspension of 3-aminophenylboronic acid. derivatized agarose beaded particles in buffered reagent solution (pH 7.7) containing 8.4 mM HEPES (N-2-hydroxyethylpiperazine-N'-2-ethanesulfonic acid), 150 mM $MgSO_4$, 0.4 g/l gentamicin sulfate and 0.05% sodium azide. More preferably the diluent buffer solution additionally contains proteinaceous stabilizers such as gelatins, albumin, casein and the like, preferably fish scale gelatin in a concentration of approximately 0.5%–5%, more preferably from 1%–2%, and most preferably 1.6%–5%; and water soluble polymers such as polyvinylpyrrolidone (PVP) (K value 90), in a concentration of approximately 0.5%–5%, more preferably from 1%–2%, and most preferably 1.6%–5%; and antimicrobial agents and preservatives such as gentamicin and sodium azide. Preferably, approximately 190 μL of the buffered reagent solution, containing approximately 65 μL of settled, hydrated beads, is used for a sample size of approximately 4–7 μL.

The buffered reagent solution and diluent buffered solution may be packaged separately, in combination as two reagents or a single reagent, more preferably as two reagents. In a preferred embodiment, the buffered reagent and diluent buffer are supplied in a device such as a test pack. Preferably each test pack contains: approximately 190 μL of buffered reagent which contains a suspension of 3-aminophenylboronic acid derivatized agarose beaded particles (3.5 mg. dry wt.) in buffer solution (pH 7.7) containing 8.4 mM HEPES (N-2-hydroxyethylpiperazine-N'-2-ethanesulfonic acid), 150 mM $MgSO_4$, 0.4 g/l gentamicin sulfate and 0.0%–5% sodium azide. The diluent buffer is approximately 140 μl of a buffer solution (pH 9.6) containing stabilizers and antimicrobial agents in the following concentrations: 94.2 mM taurine (2-aminoethylsulfonic acid), 1.6%–5% fish scale gelatin, 1.6%–5% polyvinylpyrrolidone (K value 90), 0.4 g/l gentamicin sulfate, and 0.0%–5% sodium azide.

Boronate-derivatized agarose tends to aggregate at high pH, as is used under final assay conditions. This makes the material difficult to handle and dispense. To solve this problem, the reagent system is provided in a sealed two-compartment device within a test pack. One compartment contains the boronate-agarose in a buffer of lower pH (buffered reagent) and the other compartment contains the diluent buffered solution. The contents of the two compartments are combined only at the time that the assay is run, at which point the pH of the boronate agarose is raised to the final assay pH. Those skilled in the art will recognize that the components may be added individually or in combination, in sequence or simultaneously to the sample. In a preferred embodiment, the buffered reagent solution and the diluent buffer solution are added simultaneously to the sample. In another preferred embodiment, the diluent is added to the sample followed by the buffered reagent solution.

Preferably the kit also includes, as a third separate component, a lysing agent for the sample such as a capillary tube containing dry saponin.

The calibrators and controls may be supplied packaged separately, collectively in a kit or in the test kit. The calibrators preferably contain reduced glycated azido-met-hemoglobin having glycation levels within the ranges of approximately 0%–8%, 8%–16%, and 16%–30% $HbA_{1c}$. The controls preferably contain reduced glycated azido-met-hemoglobin having glycation levels within normal and abnormal patient ranges.

EXAMPLE 1

Preparation of Boronate Agarose

The agarose, CM Sepharose™ CL6B from Pharmacia, was washed with distilled water, followed by a wash with 100 mM MES (2-N-morpholino)ethanesulfonic acid) buffer pH 4.7. The agarose was suspended to 50% solids and then cooled to 0° C. under vacuum. 66 mM mAPBA (3-aminophenylboronic acid) was prepared and cooled to 0° C. under vacuum and then added to the agarose. 800 mM EDC (1-ethyl-3-(3-dimethylaminopropyl) carbodiimide hydrochloride) was prepared and added to the reaction mixture. The mixture was reacted for 1 hour at 0° C. under vacuum and then quenched with 4M sodium acetate. The mAPBA derivatized agarose was washed sequentially with 100 mM acetic acid, 50 mM NaOH/1M NaCl, 100 mM acetic acid, 50 mM NaOH/1M NaCl and then distilled water. The washed mAPBA derivatized agarose was then washed with HEPES buffer and suspended to approximately 55% solids. The pH of the final mixture was checked and adjusted to a pH of 7.7 if necessary. Calibrators were run following the method in Example 2 using the above particles in an empty test pack and a calibration curve was prepared. To obtain the correct calibration curve, the particle percent solids can be adjusted by dilution or addition of particles.

EXAMPLE 2

Glycated Hb Method Using the Abbott Vision Test Pack and Abbott Vision Analyzer A Vision Test Pack, as shown in FIG. 1, is removed from refrigerated storage. The test pack is allowed to warm up for a minimum of 30 minutes at room temperature. A capillary tube filled with dried saponin and heparin, and containing the specimen is inserted into the capillary slot of test pack. Calibrators and controls are added directly into the calibrator and control well of the test pack using a dropper device. The test packs are placed into the analyzer and the "RUN" button pressed.

The analyzer then automatically performs the following steps:

| Step | Description | Comment |
|---|---|---|
| 1. | Rotor begins to turn. Bar code is read. | Specific assay sequence is initiated. |
| 2. | Accelerate rotor to 1800 RPM. Wait 45 sec. | Lysed whole blood sample is transferred from the inserted capillary tube to centrifugation chamber (A). Cell debris is sedimented. Reagent solution and diluent buffer are transferred from the Reagent and Diluent Chambers of the Reagent/Diluent Cup (B) to the Reagent/Diluent Holding Chambers (C). Sample and reagent/diluent begin to warm to 37 C. (Calibrators and controls follow the same process from the calibrator and control well.) |
| 3. | Rotate test pack 90°. Remain in this position 250 sec. | Aliquot of whole blood supernatant is transferred to specimen holding chamber (D). Reagent and diluent are further mixed and the reagent/diluent mixture is transferred to the reaction chamber (E). Warm-up is completed. |
| 4. | Rotate test pack −90°. Remain in this position 5 sec. Select wavelength pair. Measure and store air blank. Measure and store diluent blank. | Aliquot of whole blood supernatant is transferred to specimen volumetric chamber (F). The reagent/diluent solution is transferred to cuvette (G). Agarose beads are retained by porous filter (H). |
| 5. a) | Rotate test pack 90°. Remain in this position 3 sec. | Measured volume of whole blood supernatant (F) is added to the reagent/diluent solution as the reagent/diluent solution flows from the cuvette (G) into the reaction change (E). Whole blood supernatant is briefly mixed with the reagent/diluent solution and the agarose beads by moving the mixture from the reaction chamber (E) to the cuvette (G) and back again. |
| b) | Rotate test pack −90°. | |
| c) | Remain in this position 5 sec. | |
| d) | Repeat steps 5.a–c 3 more times. | |
| 6. | Wait 15 sec. | Initial absorbance readings, proportional to total Hb conc. are taken. Readings are corrected using additional air blank reads to compensate for any optical drift. |
| 7. a) | Wait 5 sec. | |
| b) | Measure air blank. | |
| c) | Measure sample absorbance. | |
| d) | Correct sample absorbance for air blank drift. | |
| e) | Store corrected sample absorbance. | |
| f) | Repeat steps 7.a–e 2 more times. | |
| 8. a) | Rotate test pack 90°. | Whole blood supernatant is thoroughly mixed with the reagent/diluent solution and the agarose beads by moving the mixture from the reaction chamber (E) to the cuvette (G) and back again. |
| b) | Remain in this position 15 sec. | |
| c) | Rotate test pack −90°. | |
| d) | Remain in this position 5 sec. | |
| e) | Repeat steps 8.a–d 19 more times | |
| 9. a) | Wait 15 sec. | Final absorbance readings, proportional to unbound Hb conc. are taken. Readings are corrected using additional air blank reads to compensate for any optical drift. |
| b) | Measure air blank. | |
| c) | Measure sample absorbance. | |
| d) | Correct sample absorbance for air blank drift. | |
| e) | Store corrected sample absorbance. | |
| f) | Wait 5 sec. | |
| g) | Repeat steps 9.b–f 2 more times. | |
| 10. | Stop rotation. | |
| 11. | Process data. | Initial 3 sample reading are averaged and stored as $A_i$. Final 3 sample readings are averaged and stored as $A_f$. Calculations are performed according to previously described data reduction. |
| 12. | Print results. | |

EXAMPLE 3

Calibrator and Control Material Preparation

A. Preparation of azido-met-hemoglobin (bovine).

1. Bovine red blood cells were washed free of plasma with 20 mM isotonic phosphate buffered saline.

2. Cells were lysed by hypotonic shock using a 0.01M phosphate buffer and freezing/thawing.

3. Hemoglobin was concentrated via diafiltration using filters with a 10,000 molecular weight cut off to 19.5 g/dL Hb. The pH was adjusted to pH 7.2–7.8 using 2N NaOH.

4. Lipids in the Hb solution were extracted using 40 g/L Aerosil 380 (Van Waters). The mixture was stirred for 1 to 18 hours at 4° C. The mixture was centrifuged at 4° C., 4200 rpm for 10 minutes and the hemoglobin collected and filtered. The hemoglobin was diafiltered against 20 mM phosphate buffered saline using a 10,000 molecular weight filter.

5. The hemoglobin was oxidized to met-hemoglobin using 1.3X molar excess of potassium ferricyanide for 30 to 40 minutes at 2°–8° C.

6. The met-hemoglobin was converted to azido-met-hemoglobin with a 3X molar excess of sodium azide added for 15–30 minutes at 2°–8° C .

7. The material was diafiltered using a 10,000 molecular weight cutoff filter. The pH of the solution was adjusted to 7.3–7.5 and an antimicrobial agent was added.

8. The concentration was adjusted to about 19.5 g/dL hemoglobin.

9. The material was sterile filtered and stored at 2°–8° C.

B. Preparation of Glycated Hemoglobin Stock Solution

1. Anhydrous glucose was added to azido-met-hemoglobin and mixed at 2°–8° C. for 30 minutes to give a 250 mM final concentration of glucose.

2. The solution was incubated at 37° C. until the glycation level of 30%–40% was reached.

3. Solution was dialyzed at 2°–8° C. against 20 mM phosphate buffered saline using a 10,000 molecular weight filter to remove unreacted glucose ($\leq$5 mg/dl).

4. The glycated hemoglobin was concentrated by diafiltration using a 10,000 to 30,000 molecular weight cut-off filter to about 19.5 g/dL.

5. The hemoglobin-glucose adducts were stabilized by reduction with a 10X molar excess of sodium cyanoborohydride added at 2°–8° C.

6. Completion of reduction was tested by heat stressing material at 45° C. If necessary, step 5 was repeated.

7. The hemoglobin was dialyzed against phosphate buffer.

8. Hemoglobin concentration was adjusted to 19.5 g/dL.

9. pH was adjusted to 7.4. Solution was sterile filtered and stored at 2°–8° C.

C. Preparation of Non-Glycated hemoglobin Stock Solution

This solution was prepared similarly to the glycated hemoglobin stock, except that no glucose was added.

D. The final calibrator and control solutions were prepared by making admixtures of the glycated and non-glycated stock solutions.

EXAMPLE 4

Optimization of Method for Glycating Hemoglobin

The nonenzymatic hemoglobin reaction was used to develop a procedure for in vitro synthesis of liquid stable glycated hemoglobin calibrators or controls. Fresh or frozen azido-met-hemoglobin, prepared according to the method in Example 3 from bovine erythrocytes, was incubated at 37° C. for varying lengths of time with 250 mM of glucose (4.53 g of glucose in 100 mL of 19.5 g/dL azido-met-hemoglobin). Unreacted glucose was removed by gel filtration and the glycated azido-met-hemoglobin was reduced with an excess of sodium cyanoborohydride. The by-products of the reduction were removed by dialysis against 20 mM phosphate buffer saline and the total percent glycated hemoglobin was assayed by the Iso-lab Glyc-Affin Affinity Column method. The results are shown in Table 3.

TABLE 3

BOVINE HEMOGLOBIN TIME COURSE

| No. of Hours at 37° C. | Total Glycated Hemoglobin (%) |
|---|---|
| 7 | 7.47 |
| 24 | 19.76 |
| 96 | 56.33 |
| 144 | 67.26 |
| 288 | 86.53 |
| 336 | 97.16 |

TABLE 4

HUMAN HEMOGLOBIN TIME COURSE

| No. of Hours at 37° C. | Total Glycated Hemoglobin (%) |
|---|---|
| 7 | 12.75 |
| 24 | 28.2 |
| 45 | 47.45 |
| 63 | 52.95 |
| 96 | 54.35 |
| 144 | 63.0 |

Human hemoglobin was glycated in a similar fashion and the results are shown in Table 4. Using human hemoglobin which had been stored frozen, a maximum percent total glycation of 63% was observed after approximately 144 hours when the human hemoglobin began to aggregate (Table 4).

Figure 3:
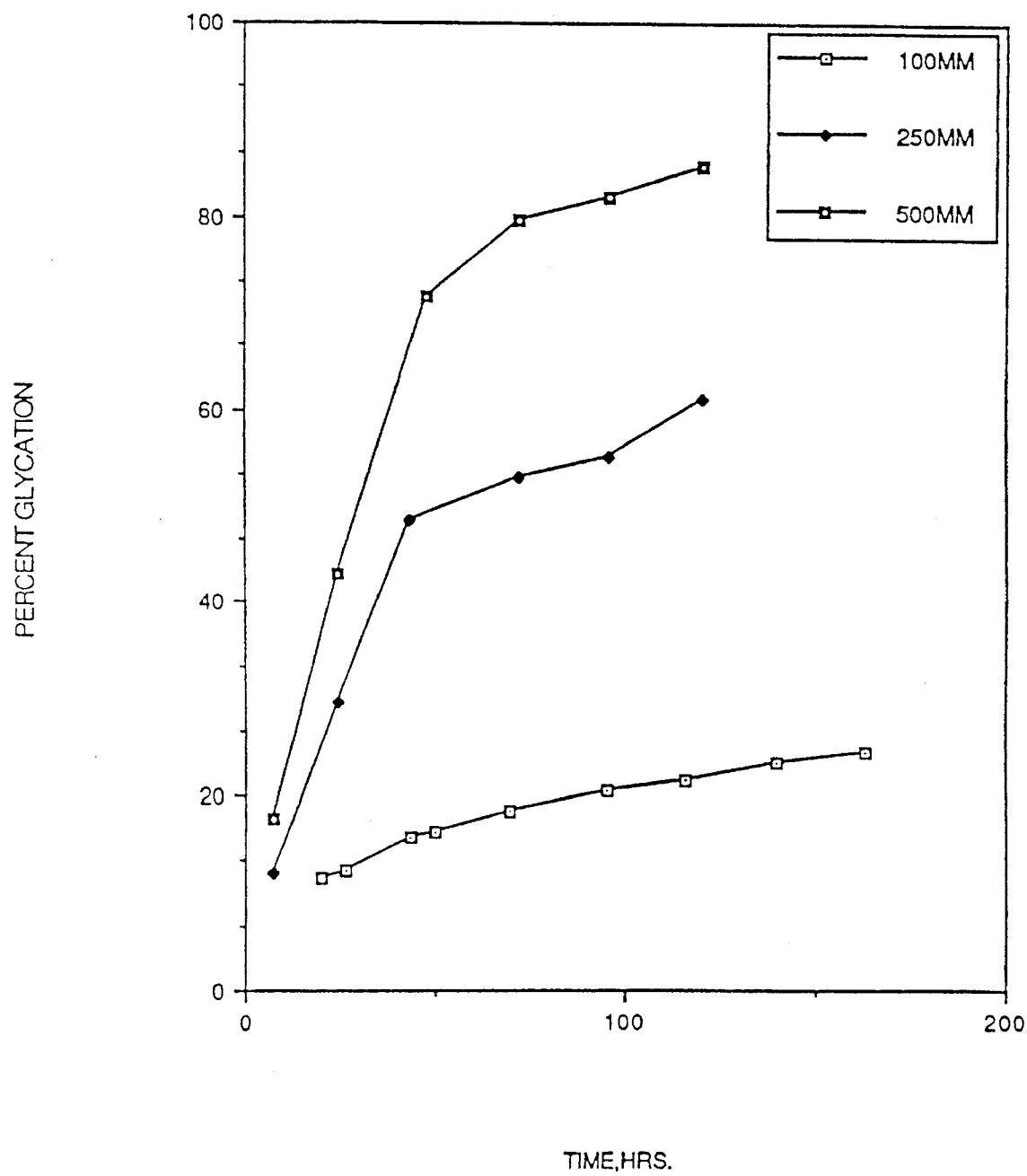
FIG. 3 is a time course study of in vitro glycation of bovine hemoglobin as a function of glucose concentration.

Time course comparisons of glucose concentration to percent total glycation with bovine hemoglobin illustrated two important factors in the glycation method (FIG. 3). First, the maximum percent glycation increased with increasing glucose concentrations and second, the rate of percent glycation was accelerated at higher glucose concentrations. Both factors contribute to optimizing the glycation process.

Figure 4:
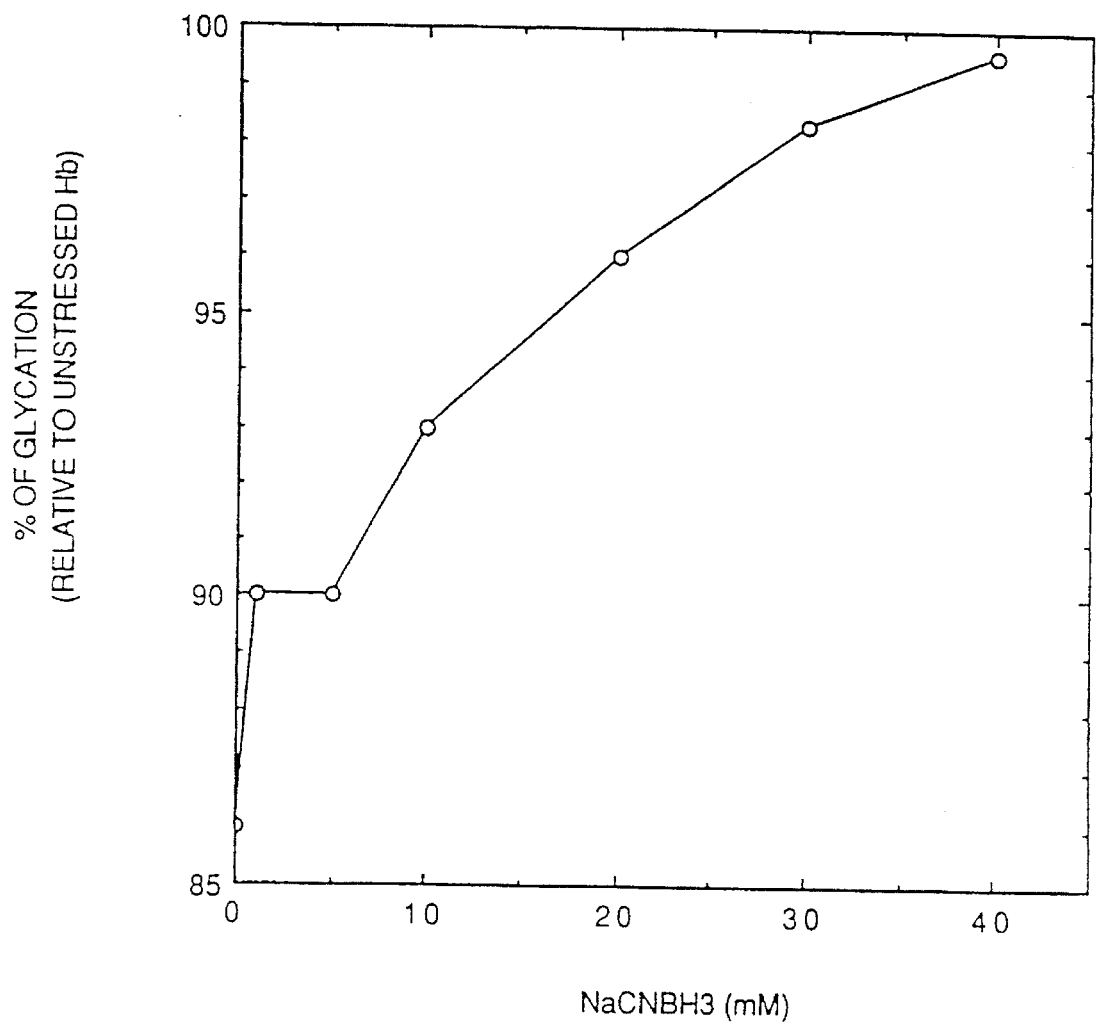
FIG. 4 shows the stabilization of glycated bovine azido-met-hemoglobin by reduction with sodium cyanoborohydride as shown by 24 hour stress at 45° C.

In order to prove that a 24 hour 45° C. heat stress is an effective predictor of the efficacy of sodium cyanoborohydride ($NaCNBH_3$) reduction, the high level calibrator was incubated at 45° C. with varying concentrations of $NaCNBH_3$. Various quantities of $NaCNBH_3$ were added to the high level calibrator, based on the concentration of heme in the calibrator, in order to effect the final concentrations shown in Table 5. Each solution was divided into two aliquots; one aliquot was incubated at 45° C. for 24 hours and the other aliquot was stored at 2°–8° C. The data from this experiment is shown in Table 5 and depicted in FIG. 4. This experiment demonstrates the efficacy of the $NaCHBH_3$ reduction for stabilization of glycated hemoglobin when present in the appropriate amounts and the efficacy of a 45° C. heat stress to be used as a monitor or control for the $NaCNBH_3$ reduction.

TABLE 5

Glycated Hemoglobin Stability: 24 Hour 45° C. Heat Stress

| mM Concentration $NaCNBH_3$ | 2–8° C. Control | 24 hr. 45° C. Stressed | % Diff. |
|---|---|---|---|
| 0 mM | 14.68% | 12.69% | –14.0% |
| 1 mM | *13.99% | 12.63% | –10.0% |
| 5 mM | 14.55% | 13.14% | –10.0% |
| 10 mM | 14.66% | 13.60% | –7.0% |
| 20 mM | 14.74% | 14.14% | –4.0% |
| 30 mM | 14.85% | 14.60% | –1.68% |
| 40 mM | 14.94% | 14.88% | –0.40% |

*Indicates a leaky column.

Figure 5:
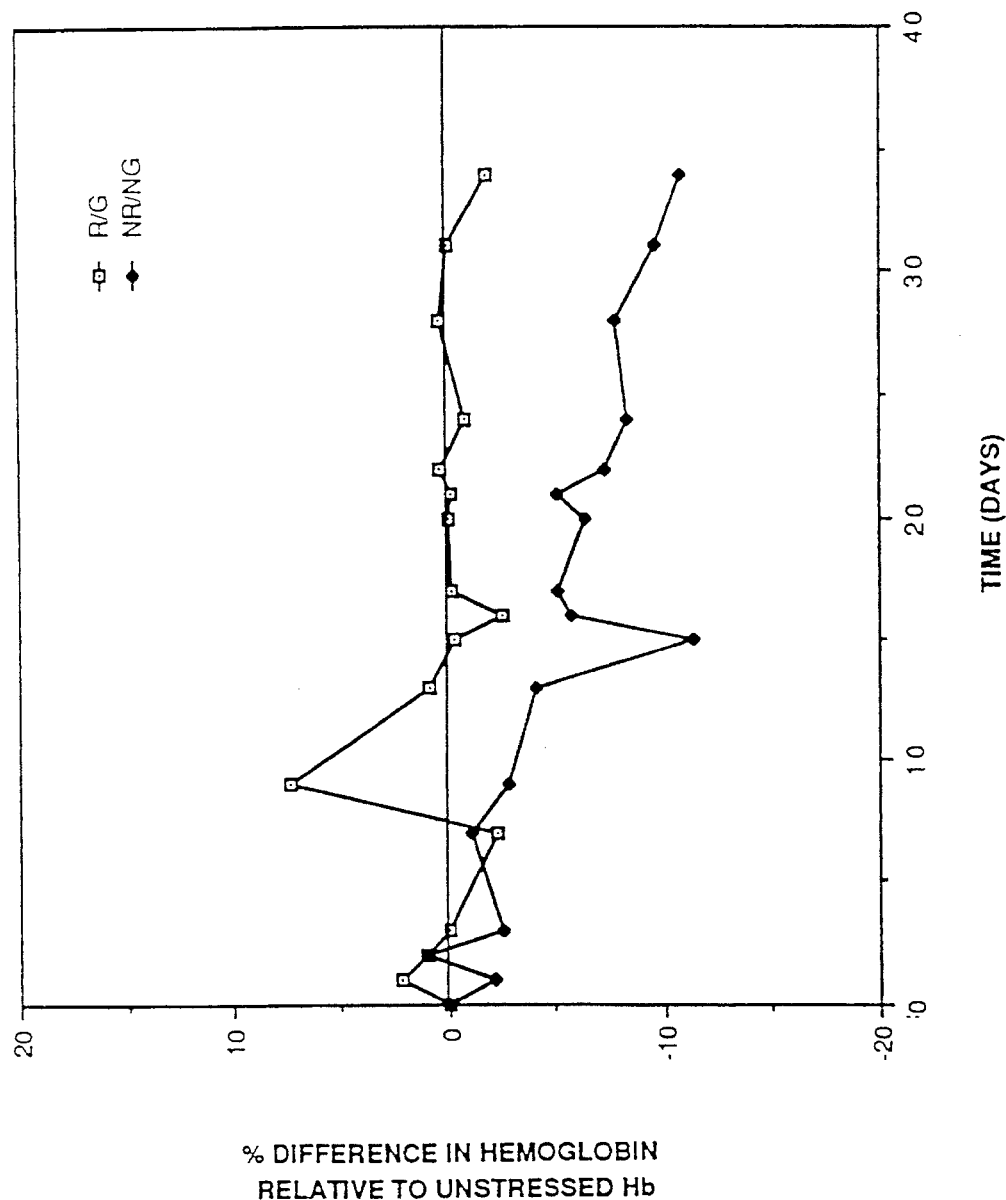
FIG. 5 shows the stability of hemoglobin that is glycated and reduced vs. hemoglobin that is non-glycated and non-reduced.

In order to prove that sodium cyanoborohydride reduction of glycated bovine azido-met-hemoglobin increases the stability of the hemoglobin (Hb) as compared to the stability of nonglycated, nonreduced azido-met-hemoglobin, an aliquot of each at a concentration of approximately 17.5 g/dl Hb for the glycated, reduced sample, and 18.1 g/dl for the nonglycated, nonreduced sample, were incubated at 45° C. and a control of the same concentration was stored at 2°–8° C. A sample of each was periodically taken at intervals for 34 days and the hemoglobin concentration measured. The results in Table 6 and FIG. 5 show that the glycated, reduced bovine azido-met-hemoglobin is more stable than the nonglycated, nonreduced form.

Figure 6A:
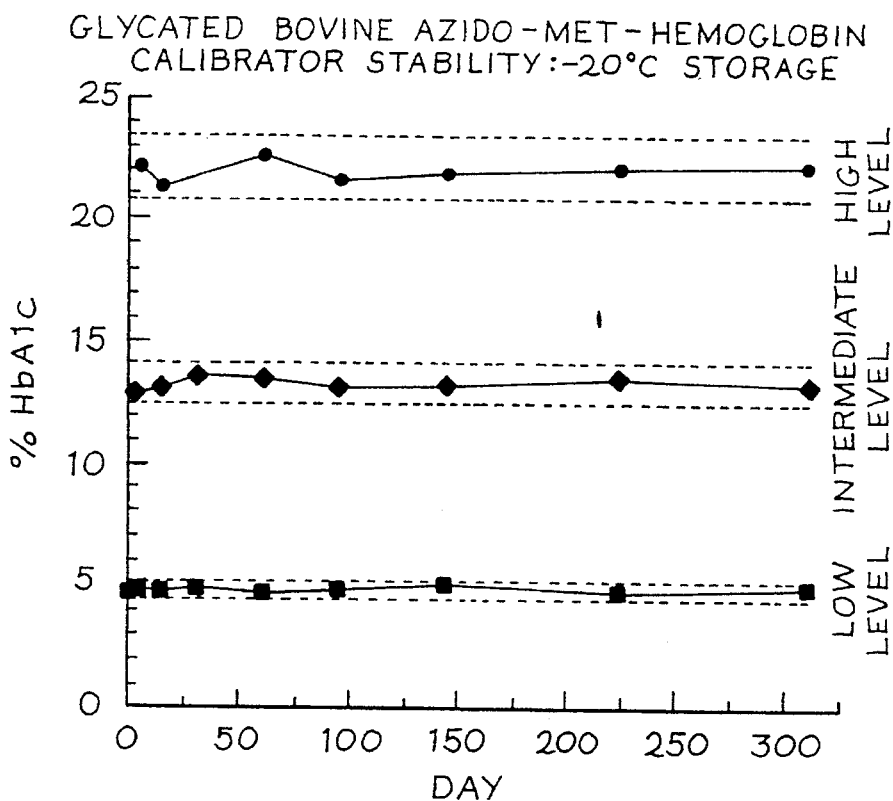
FIG. 6 shows the longterm stability of glycated bovine azido-met-hemoglobin calibrator material stored at −20° C. and 2°–8° C. Calibrator A=4.4%–5.0% glycated hemoglobin ($HbA_{1c}$); Calibrator B=12.4%–14.0% $HbA_{1c}$; Calibrator C=20.7%–23.3% $HbA_{1c}$.
Figure 6B:
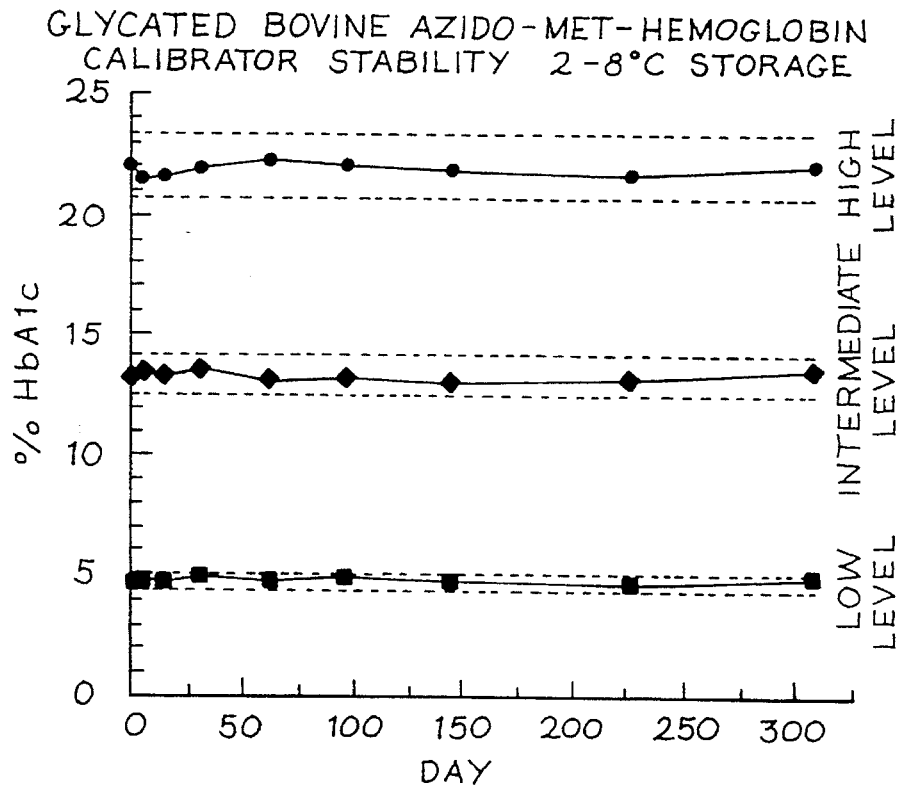

The long term stability of the reduced form of the glycated bovine azido-met-hemoglobin calibrators was determined by incubation at −20° C. and at 2°–8° C. An aliquot of each of the standards was tested daily for percent $HbA_{1c}$ for a total of 309 days. The results in Table 7 and FIG. 6 show that the calibrators are stable for prolonged periods of storage at either −20° C. or 2°–8° C. No adverse effects were noted.

TABLE 7-continued

LONG TERM STABILITY OF "STABILIZED" CALIBRATOR MATERIAL

| DAY | 4.4–5.0* CAL A | 12.4–14.0* CAL B | 20.7–23.3* CAL C |
| --- | --- | --- | --- |
| 61 | 4.86 | 13.02 | 22.08 |
| 95 | 4.90 | 13.10 | 21.90 |
| 144 | 4.84 | 12.91 | 21.76 |
| 224 | 4.66 | 13.04 | 21.47 |
| 309 | 4.79 | 13.29 | 21.82 |

*% $HbA_{1c}$

TABLE 6

HEMOGLOBIN ACCELERATED HEAT STRESS EXPERIMENT
Comparison of Hemoglobin Stability
Glycated/Reduced v. Nonglycated/Nonreduced Hb

| Days | Reduced/Glycated 2–8c Hb [ ] | Reduced/Glycated 45 Hb [ ] | % Difference R/G 45c vs. 2–8c | Nonreduced/ Nongly. 2–8c Hb [ ] | Nonreduced/ Nongly. 45c Hb [ ] | % Difference NR/NG 45c vs. 2–8c |
| --- | --- | --- | --- | --- | --- | --- |
| 0 | 17.47 g/dl | x | x | 18.13 g/dl | x | x |
| 1 | 17.65 g/dl | 18.03 g/dl | 2.15% | 18.25 g/dl | 17.87 g/dl | −2.08% |
| 2 | 17.60 g/dl | 17.77 g/dl | 0.97% | 17.95 g/dl | 18.13 g/dl | 1.00% |
| 3 | 17.80 g/dl | 17.80 g/dl | 0.00% | 18.10 g/dl | 17.65 g/dl | −2.49% |
| 7 | 17.90 g/dl | 17.50 g/dl | −2.23% | 18.05 g/dl | 17.85 g/dl | −1.11% |
| 9 | 17.05 g/dl | 18.30 g/dl | 7.33% | 18.30 g/dl | 17.80 g/dl | −2.73% |
| 13 | 18.25 g/dl | 18.40 g/dl | 0.82% | 18.65 g/dl | 17.90 g/dl | −4.02% |
| 15 | 17.95 g/dl | 17.90 g/dl | −0.28% | 18.50 g/dl | 16.40 g/dl | −11.35% |
| 16 | 18.37 g/dl | 17.90 g/dl | −2.56% | 18.47 g/dl | 17.40 g/dl | −5.79% |
| 17 | 18.33 g/dl | 18.30 g/dl | −0.16% | 18.57 g/dl | 17.63 g/dl | −5.06% |
| 20 | 18.07 g/dl | 18.07 g/dl | 0.00% | 18.27 g/dl | 17.10 g/dl | −6.40% |
| 21 | 18.10 g/dl | 18.07 g/dl | −0.17% | 18.20 g/dl | 17.27 g/dl | −5.11% |
| 22 | 17.75 g/dl | 17.80 g/dl | 0.28% | 18.35 g/dl | 17.00 g/dl | −7.36% |
| 24 | 18.25 g/dl | 18.10 g/dl | −0.82% | 18.60 g/dl | 17.05 g/dl | −8.33% |
| 28 | 18.05 g/dl | 18.10 g/dl | 0.28% | 18.40 g/dl | 16.95 g/dl* | −7.88% |
| 31 | 17.95 g/dl | 17.95 g/dl | 0.00% | 18.60 g/dl | 16.80 g/dl | −9.68% |
| 34 | 18.15 g/dl | 17.80 g/dl | −1.93% | 18.45 g/dl | 16.45 g/dl | −10.84% |

Note: NR/NG = Nonreduced/Nonglycated
Note: R/G = Reduced/Glycated
*Observed macroscopic agglutination in NR/NG

TABLE 7

LONG TERM STABILITY OF "STABILIZED" CALIBRATOR MATERIAL

| DAY | 4.4–5.0* CAL A | 12.4–14.0* CAL B | 20.7–23.3* CAL C |
| --- | --- | --- | --- |
| CALIBRATORS STORED AT −20° C. | | | |
| 4 | 4.89 | 12.78 | 22.02 |
| 14 | 4.63 | 13.02 | 21.29 |
| 31 | 4.78 | 13.54 | 21.71 |
| 61 | 4.62 | 13.44 | 22.44 |
| 95 | 4.70 | 13.00 | 21.40 |
| 144 | 4.91 | 12.96 | 21.69 |
| 224 | 4.62 | 13.35 | 21.92 |
| 309 | 4.72 | 13.15 | 22.02 |
| CALIBRATORS STORED AT 2–8° C. | | | |
| 1 | 4.70 | 13.18 | 22.01 |
| 4 | 4.75 | 13.28 | 21.32 |
| 14 | 4.68 | 13.20 | 21.49 |
| 31 | 4.88 | 13.52 | 21.83 |

EXAMPLE 5

EXPECTED VALUES

Using the method of the present invention, the glycated hemoglobin reference range was determined to be 4.1 to 5.7 standardized %$HbA_{1c}$. This range was confirmed by testing 101 apparently healthy individuals (41 females, 60 males). Reference ranges may vary depending on the specific patient populations.

EXAMPLE 6

REPRODUCIBILITY

Reproducibility of the method of the present invention was determined by field testing two levels of glycated hemoglobin controls in replicates of four over 5 days using one analyzer. The grand mean and Coefficient of Variation (%CV) were calculated from an analysis of variance. The total %CV combines contributions from both within and between day variation.

| ABBOTT VISION Glycated Hb Controls | Mean % HbA$_{1c}$ | Within Day % CV | Total % CV |
|---|---|---|---|
| Control I | 5.3 | 3.2 | 3.2 |
| Control II | 10 | 2.2 | 2.6 |

EXAMPLE 7

ACCURACY

Accuracy of the present method for determining the percent glycated Hb test was determined by comparison of this test with the HPLC Glycated hemoglobin assay or the Isolab Glycaffin assay (total glycated hemoglobin by affinity) in field testing of human whole blood specimens. A correlation study between the method of the present invention for determining percent glycated hemoglobin and the method HPLC method for glycated hemoglobin was conducted.

The present method for determining glycated hemoglobin was Derformed in a physician's office environment by physician's office personnel using 51 human whole blood specimens ranging in glycated hemoglobin values from 4.5% to 13.3% The results were correlated with those results obtained using the HPLC Glycated Hemoglobin method.

Figure 7:
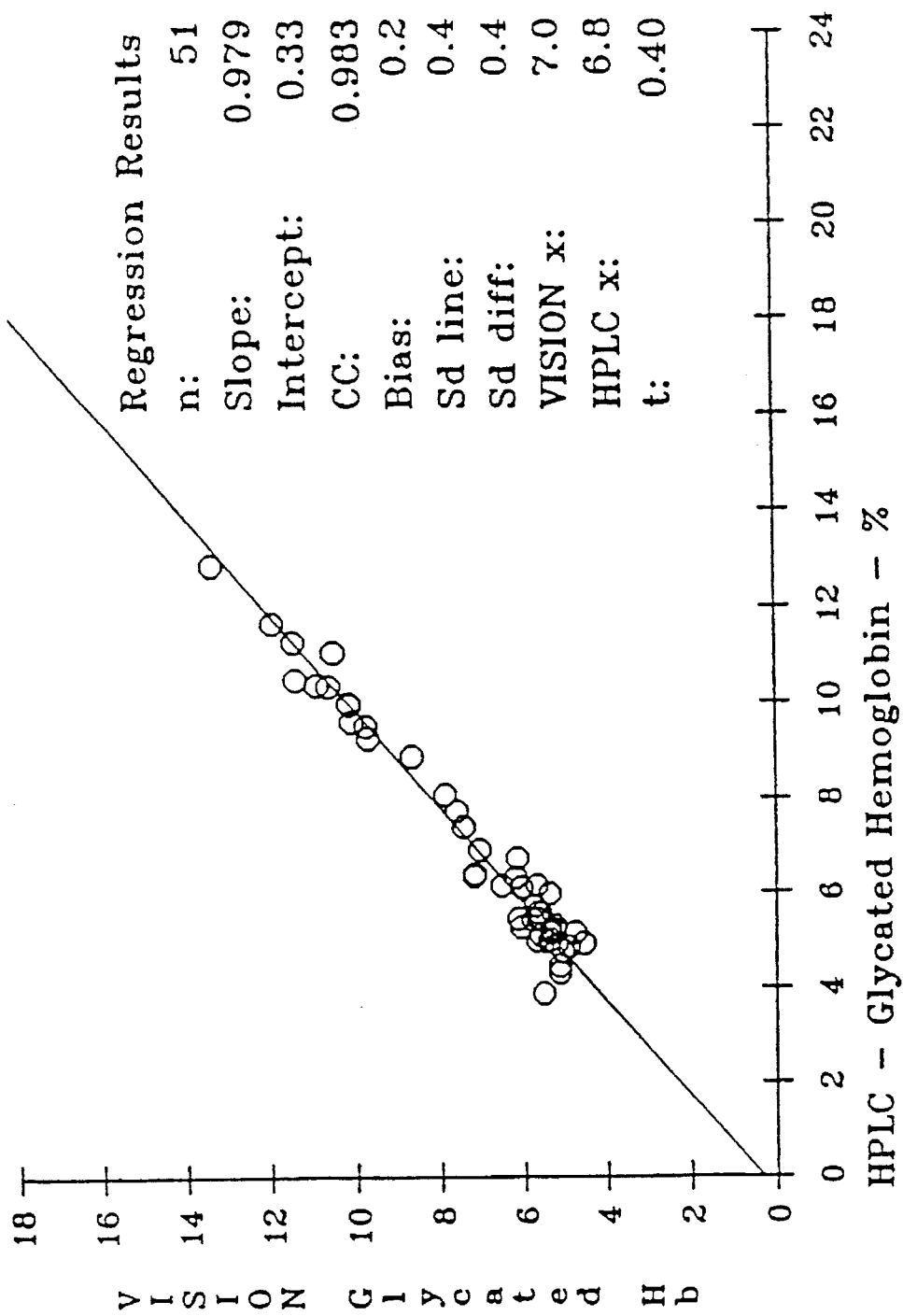
FIG. 7 shows the correlation between the method of the present invention and the HPLC-Glycated Hb method. The correlation coefficient (CC)=0.979.

All specimens were assayed in the field in singlet. Correlation of the VISION Glycated Hb system with the HPLC Glycated Hemoglobin system is reported in FIG. 7. Linear regression analysis gave the following results:

Comparison: VISION Glycated Hb (Y axis) vs. HPLC Glycated Hemoglobin (X axis)

Number of samples=51

Slope=0.98

Intercept=0.33

Correlation Coefficient=0.983

Bias=0.2

Sd Line=0.4

Sd. diff.=0.4 t=0.40

No statistically or clinically significant differences observed.

The following correlations were observed using the method of the present invention for glycated hemoglobin vs Isolab Glycaffin test:

N=51

Slope=0.652

Intercept=1.40

Correlation Coefficient=0.991

Bias=−1.6

Sd line=0.3

Sd Diff.=1.3

Paired t=−8.97

Non Paired t=−2.69

Figure 8:
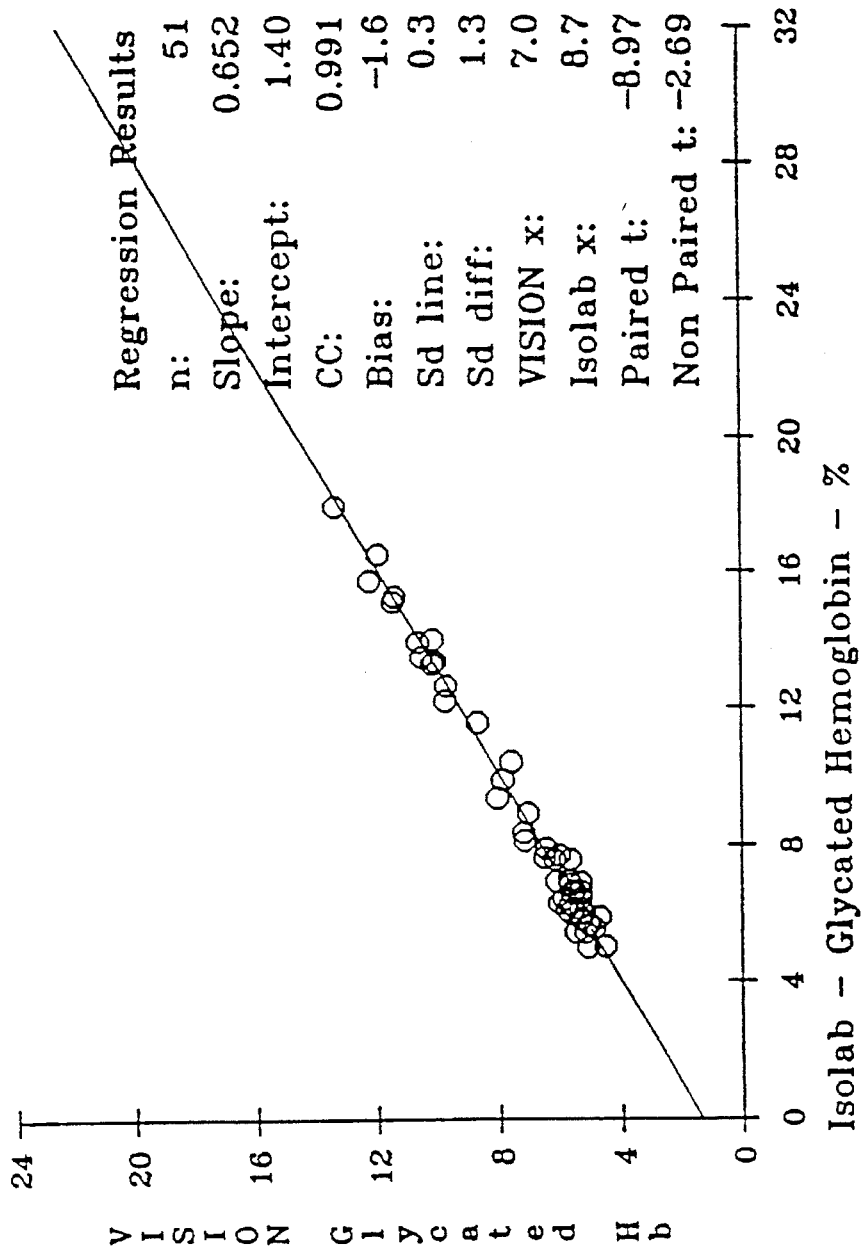
FIG. 8 shows the correlation between the method of the present invention and the Isolab Glyc-Affin hemoglobin assay. The correlation coefficient (CC)=0.991.

These data are plotted in FIG. 8.

EXAMPLE 8

INTERFERENCES

The following commonly prescribed drugs have been checked for interference with the method of the present invention by testing whole blood samples containing the added substance. The following substances, at the given concentration, showed less than 10% interference with samples containing the specified levels of HbA$_{1c}$:

| Test Substance | Concentration | % HbA$_{1c}$ |
|---|---|---|
| ENDOGENOUS SUBSTANCES | | |
| Bilirubin | 30 mg/dl | 4.7 |
| Glucose | 800 mg/dl | 4.5 |
| Triglycerides | 1300 mg/dl | 4.8 |
| DRUGS PRESCIBED FOR TYPE II DIABETES | | |
| Chlorpropamide | 75 mg/dl | 5.5 |
| Glipizide | 50 mg/dl | 5.5 |
| Glyburide | 50 mg/dl | 5.5 |
| Tolbutamide | 100 mg/dl | 5.8 |

The following substances did not significantly interfere with the method at the specimen concentration listed. Significant interference is defined as more than a 10% shift in the test result for a normal range specimen.

| COMMONLY PRESCRIBED DRUGS | CONCENTRATION TESTED |
|---|---|
| Acetaminophen (Tylenol) | 30 mg/dl |
| Acetylsalicylic Acid (Aspirin) | 50 mg/dl |
| Ascorbic Acid (Vitamin C) | 10 mg/dl |
| Caffeine | 6 mg/dl |
| Cefoxitin | 2.5 mg/dl |
| Cimetidine (Tagamet) | 7.5 mg/dl |
| L-Dopa | 10 mg/dl |
| Epinephrine (Adrenalin) | 0.1 mg/dl |
| Hydrochlorothiazide | 5 mg/dl |
| Isoniazid | 2.5 mg/dl |
| Penicillin G | 1000 Units/dl |
| Phenytoin (Dilantin) | 8 mg/dl |
| Salicylic Acid | 40 mg/dl |
| Theophylline | 8 mg/dl |
| Warfarin (Coumadin) | 10 mg/dl |

EXAMPLE 9

HEMOGLOBIN VARIANTS (ABNORMAL HEMOGLOBINS)

Affinity binding methods for glycated hemoglobin show minimal interference due to hemoglobin variants (Middle, F. A. et al., Biochem. J. 209:771–779, 1983; Abraham, E. C. et al., J. Lab. Clin. Med. 102:187–197, 1983; Talwar, D. et al., Clin. Chem. Acta 128:61–67, 1983; Yatscoff, R. W. et al., Clin. Chem. 29:543–545, 1983). Hemoglobins F (fetal), S, and C have been determined not to interfere with the test described in this invention. It is assumed, by analogy, that other variants also do not interfere.

What is claimed is:

1. A method for preparing a stable glycated hemoglobin solution useful as a calibrator or control in an assay for glycated hemoglobin comprising:

a. washing erythrocytes;

b. releasing hemoglobin from the erythrocytes into a solution;

c. removing lipids from the hemoglobin solution;

d. oxidizing the hemoglobin to met-hemoglobin;

e. converting the met-hemoglobin to azido-met-hemoglobin or cyano-met-hemoglobin; and f. adding glucose to the azido-met-hemoglobin or cyanomethemoglobin to form glycated azido-met-hemoglobin or glycated cyano-met-hemoglobin.

2. The method of claim 1 wherein the erythrocytes are mammalian erythrocytes.

3. The method of claim 1 wherein the hemoglobin is oxidized to met-hemoglobin using potassium ferricyanide.

4. The method of claim 1 wherein the met-hemoglobin is converted to azido-met-hemoglobin using sodium azide.

5. The method of claim 1 wherein the met-hemoglobin is converted to cyano-met-hemoglobin using a cyanide salt.

6. The method of claim 1 further comprising reducing the glycated azido-met-hemoglobin or glycated cyano-met-hemoglobin using a reducing agent.

7. The method of claim 6 wherein the reducing agent is sodium cyanoborohydride.

8. The method of claim 6 wherein the completion of the reduction is tested by elevated heat-stress testing.

* * * * *

UNITED STATES PATENT AND TRADEMARK OFFICE
CERTIFICATE OF CORRECTION

PATENT NO. : 5,589,393
DATED : December 31, 1996
INVENTOR(S) : Fiechtner, et. Al.

It is certified that error appears in the above-indentified patent and that said Letters Patent is hereby corrected as shown below:

Column 22, line 66, change "methemoglobin" to --met-hemoglobin--.

Signed and Sealed this

Tenth Day of June, 1997

Attest:

BRUCE LEHMAN

Attesting Officer     Commissioner of Patents and Trademarks